US00PP20636P2

(12) United States Plant Patent
Hodson

(10) Patent No.: US PP20,636 P2
(45) Date of Patent: Jan. 12, 2010

(54) ***ERYNGIUM* PLANT NAMED 'BIG BLUE'**
(50) Latin Name: *Eryngium zabelii*
Varietal Denomination: Big Blue

(75) Inventor: Jeff Hodson, Preston (GB)

(73) Assignee: Myerscough College of Preston, Lancashire (GB)

( * ) Notice: Subject to any disclaimer, the term of this patent is extended or adjusted under 35 U.S.C. 154(b) by 0 days.

(21) Appl. No.: 12/287,358

(22) Filed: Oct. 8, 2008

(51) Int. Cl.
*A01H 5/00* (2006.01)

(52) U.S. Cl. ..... Plt./361
(58) Field of Classification Search ..... Plt./361
See application file for complete search history.

*Primary Examiner*—Kent L Bell
(74) *Attorney, Agent, or Firm*—C. A. Whealy

(57) ABSTRACT

A new and distinct cultivar of *Eryngium* plant named 'Big Blue', characterized by its upright and columnar plant habit; strong thick stems; relatively large violet blue-colored flowers on dense flower heads; and good garden performance.

1 Drawing Sheet

Botanical designation: *Eryngium zabelii*. Cultivar denomination: 'Big Blue'.

BACKGROUND OF THE INVENTION

The present invention relates to a new and distinct cultivar of *Eryngium* plant, botanically known as *Eryngium zabelii*, and hereinafter referred to by the name 'Big Blue'.

The new *Eryngium* plant originated from a chance open-pollination in Preston, Lancashire, United Kingdom of an unnamed selection of *Eryngium zabelii*, not patented, as the female, or seed, parent with an unknown selection of *Eryngium zabelii* as the male, or pollen, parent. The new *Eryngium* was discovered and selected by the Inventor as a single flowering plant within the progeny of the stated open-pollination in a controlled outdoor nursery environment in Preston, Lancashire, United Kingdom in June, 1997.

Asexual reproduction of the new *Eryngium* plant by cuttings in a controlled environment in Preston, Lancashire, United Kingdom since February, 1998, has shown that the unique features of this new *Eryngium* plant are stable and reproduced true to type in successive generations.

SUMMARY OF THE INVENTION

Plants of the new *Eryngium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Big Blue'. These characteristics in combination distinguish 'Big Blue' as a new and distinct cultivar of *Eryngium*:

1 . Upright and columnar plant habit.
2 . Strong thick stems.
3. Relatively large violet blue-colored flowers on dense flower heads.
4. Good garden performance.

Plants of the new *Eryngium* differ from plants of the female parent selection primarily in plant size as plants of the new *Eryngium* are more compact than plants of the female parent selection.

Plants of the new *Eryngium* can also be compared to plants of the *Eryngium zabelii* 'Sapphire Blue', disclosed in U.S. Plant Pat. No. 11,088. Plants of the new *Eryngium* differ from plants of 'Sapphire Blue' in the following characteristics:

1. Plants of the new *Eryngium* had larger flowers than plants of 'Sapphire Blue'.
2. Plants of the new *Eryngium* and 'Sapphire Blue' differed in flower color as plants of 'Sapphire Blue' had dark violet blue-colored flowers.

BRIEF DESCRIPTION OF THE PHOTOGRAPHS

The accompanying photographs illustrate the overall appearance of the new *Eryngium* plant. The photographs show the colors as true as it is reasonably possible to obtain in colored reproductions of this type. Colors in the photographs may differ slightly from the color values cited in the detailed botanical description which accurately describe the colors of the new *Eryngium* plant.

The photograph at the bottom of the sheet comprises a side perspective view of a typical flowering plant of 'Big Blue' grown in a container.

The photograph at the top of the sheet is a close-up view of typical inflorescences of 'Big Blue'.

DETAILED BOTANICAL DESCRIPTION

The aforementioned photographs and following observations and measurements describe plants grown in Lancaster, Pa. during the summer in one-gallon containers in a polyethylene-covered greenhouse and under conditions and practices which approximate those generally used in commercial *Eryngium* production. During the production of the plants, day and night temperatures ranged from 2° C. to 18° C. Measurements and numerical values represent averages for typical flowering plants. Plants had been growing for four months when the photographs and description were taken. In the following description, color references are made to The Royal Horticultural Society Colour Chart, 2001 Edition, except where general terms of ordinary dictionary significance are used.

Botanical classification: *Eryngium zabelii* 'Big Blue'.

Parentage:

*Female, or seed, parent.*—Unnamed selection of *Eryngium zabelii*, not patented.

*Male, or pollen, parent.*—Unknown selection of *Eryngium zabelii*, not patented.

Propagation:

*Type.*—By cuttings.

*Time to initiate roots.*—About one month at 20° C. to 25° C.

*Time to produce a rooted young plant.*—About two months at 20° C. to 25° C.

*Root description.*—Fleshy, medium thickness; greyed white in color.

*Rooting habit.*—Moderate branching; moderately dense.

Plant description:

*Plant form/growth habit.*—Herbaceous perennial; upright and columnar plant habit; moderately vigorous growth habit; strong, thick stems.

*Plant height.*—About 47 cm.

*Plant diameter or spread.*—About 24 cm.

*Stem description.*—Length: About 47 cm. Diameter: About 8 mm. Internode length: About 6.3 cm. Aspect: Upright. Strength: Strong. Texture: Smooth, glabrous; longitudinally ridged. Color: Longitudinal stripes, 191A and 192B; tinged with 92B to 92C.

Foliage description:

*Arrangement.*—Alternate, simple.

*Length.*—About 9 cm.

*Width.*—About 14.4 cm.

*Shape.*—Palmately lobed.

*Apex.*—Acuminate.

*Base.*—Cordate.

*Margin.*—Bi-serrate, erose; undulate. Prickles at margin, about 2mm in length and close to 158A in color.

*Texture, upper and lower surfaces.*—Smooth, glabrous; leathery.

*Venation pattern.*—Palmatifid, reticulate.

*Color.*—Developing leaves, upper surface: Close to 137A. Developing leaves, lower surface: Close to 137C. Fully expanded leaves, upper surface: Close to N137C; venation, close to 157A. Fully expanded leaves, lower surface: Close to 147B; venation, close to 157A.

*Petioles.*—Length: About 14.3 cm. Diameter: About 4 mm. Texture, upper and lower surfaces: Smooth, glabrous. Color, upper surface: Close to 138B. Color, lower surface: Longitudinal stripes, close to 138B and 157A.

Flower description:

*Flower arrangement and habit.*—Single rotate flowers arranged on dense cylindrical flower heads; flowers sessile. Inflorescences terminal or arising from leaf axils. Freely flowering habit with usually about 120 flowers developing per inflorescence. Flowers face upright and outwardly.

*Fragrance.*—Not detected.

*Natural flowering season.*—Plants of the new *Eryngium* flower from mid-June through July in Pennsylvania.

*Flower longevity.*—Flowers last about three weeks on the plant and about two weeks as a cut flower; flowers persistent.

*Inflorescence height.*—About 2.7 cm.

*Inflorescence diameter, without involucral bracts.*—About 2.2 cm.

*Inflorescence diameter, with involucral bracts.*—About 7.3 cm.

*Flower diameter.*—About 4 mm.

*Flower length (depth).*—About 1.1 cm.

*Flower bud.*—Shape: Obovate. Length: About 3 mm. Diameter: About 1.5 mm. Color: Close to 145B.

*Petals.*—Arrangement: Five petals in a single whorl. Length: About 2.5 mm. Width: About 1 mm. Shape: Oblong. Apex: Emarginate. Base: Truncate. Margin: Entire. Texture, upper and lower surfaces: Smooth, glabrous. Color: When opening, upper and lower surfaces: Close to NN155C; towards the apex, close to 91B. Fully opened, upper and lower surfaces: Close to NN155C; towards the apex, close to 91B.

*Sepals.*—Arrangement: Five sepals in a single whorl. Length: About 2 mm. Width: About 1 mm. Shape: Lanceolate. Apex: Acuminate to spinose Base: Fused. Margin: Entire. Texture, upper and lower surfaces: Smooth, glabrous. Color, immature, upper and lower surfaces: Close to 137A. Color, mature, upper and lower surfaces: Close to 137A.

*Inflorescence bracts.*—Arrangement: About eight bracts in a single whorl subtending the flower head. Length: About 3 cm. Width: About 4 mm. Shape: Lanceolate; spinose. Apex: Apiculate. Base: Truncate. Margin: Spinous. Texture, upper and lower surfaces: Smooth, glabrous; rigid. Color, immature and mature, upper and lower surfaces: Close to 96B to 96C.

*Peduncles.*—Length, terminal peduncles: About 8.8 cm. Length, lateral peduncles: About 5.6 cm. Diameter, terminal and lateral peduncles: About 4 mm. Angle: Main peduncle, erect; lateral peduncles, about 45° to 55° from vertical. Strength: Strong. Texture: Smooth, glabrous; longitudinally ridged. Color: Close to 96C.

*Reproductive organs.*—Stamens: Quantity/arrangement: About five per flower. Filament length: About 2 mm. Filament color: Close to 97D. Anther shape: Oblong. Anther length: About 1 mm. Anther color: Close to 95C. Pollen amount: Scarce. Pollen color: Close to 95D. Pistils: Quantity: About two per flower. Pistil length: About 1 cm. Style length: About 7 mm. Style color: Close to 95D. Stigma shape: Rounded. Stigma color: Close to 95D. Ovary color: Close to 145B.

*Fruits/seeds.*—Fruit and seed development have not been observed.

Disease/pest resistance: Plants of the new *Eryngium* have not been shown to be resistant to pathogens and pests common to *Eryngium*.

Garden performance: Plants of the new *Eryngium* have exhibited good tolerance to rain and wind, have been observed to tolerate temperatures from USDA Hardiness Zones 5 to 9 and AHS Heat Zones 8 to 5.

It is claimed:

1. A new and distinct *Eryngium* plant named 'Big Blue' as illustrated and described.

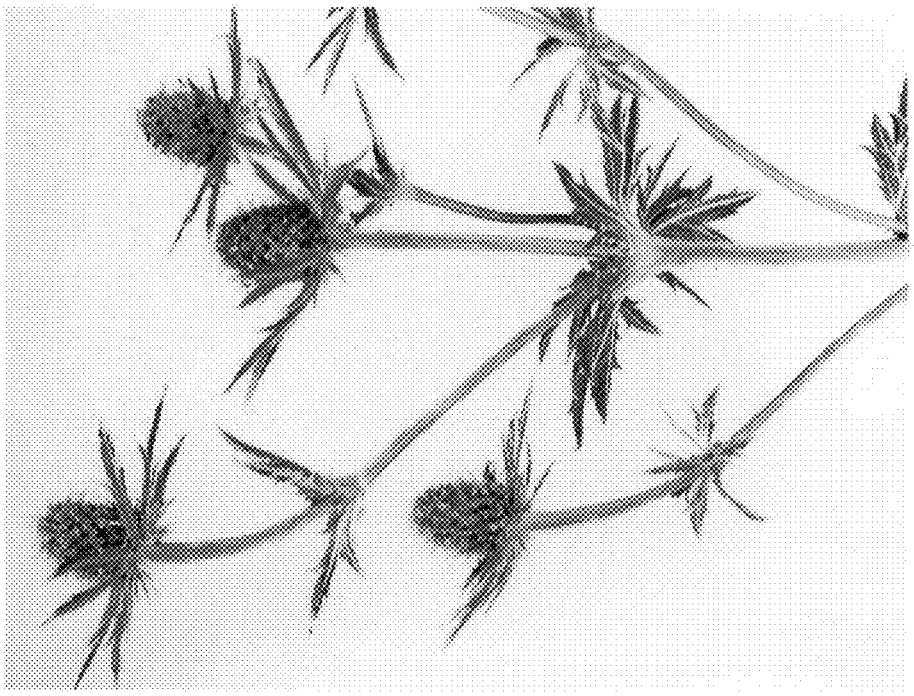
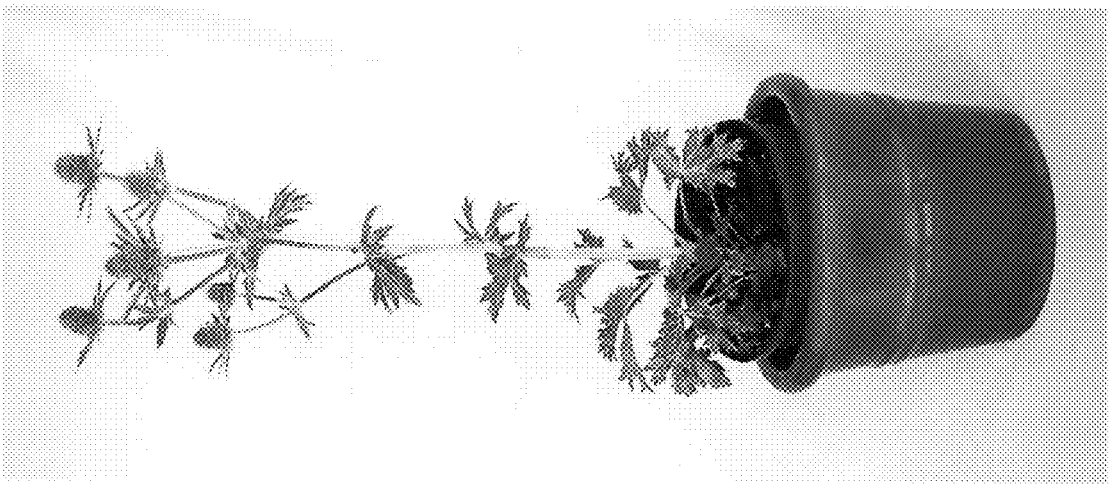

* * * * *